United States Patent [19]
Cohen et al.

[11] Patent Number: 5,206,159
[45] Date of Patent: Apr. 27, 1993

[54] POLYMER PARTICLES CONTAINING COLLOIDAL IRON OXIDE GRANULES FOR USE AS A MAGNETICALLY RESPONSIVE REAGENT CARRIER

[75] Inventors: Beri Cohen, White Plains, N.Y.; Tak K. Wong, Hamden, Conn.; Bartholomew Hargitay, White Plains, N.Y.

[73] Assignee: Miles Inc., as Legal Successor by Merger with Technicon Instruments Corp., Tarrytown, N.Y.

[21] Appl. No.: 934,287

[22] Filed: Aug. 25, 1992

Related U.S. Application Data

[63] Continuation of Ser. No. 676,010, Mar. 27, 1991, abandoned, which is a continuation of Ser. No. 53,562, May 21, 1987, abandoned.

[51] Int. Cl.$^5$ .................. C12N 11/08; C12Q 1/00; G01N 33/53; G01N 33/545
[52] U.S. Cl. .................. 435/180; 252/62.54; 252/62.56; 435/4; 435/7.92; 435/174; 435/176; 436/531; 436/534
[58] Field of Search .................. 435/174, 176, 180, 4, 435/7.92; 436/526, 531, 532, 533, 534; 252/62.54, 62.56

[56] References Cited

U.S. PATENT DOCUMENTS

| | | | |
|---|---|---|---|
| 4,297,337 | 10/1981 | Mansfield et al. | 424/1 |
| 4,335,094 | 6/1982 | Mosbach | 424/1 |
| 4,474,866 | 10/1984 | Ziolo | 430/106.6 |
| 4,654,267 | 3/1987 | Ugelsbad et al. | 428/407 |
| 4,774,265 | 9/1988 | Ugelstad et al. | 521/55 |

OTHER PUBLICATIONS

Magnetic Support for Affinity Reactions in Hetcrogeneous Phase, Magnogel 44, L'Industrie Biologique Francaise Feb., 1979, pp. 2-7.

*Primary Examiner*—David M. Naff
*Attorney, Agent, or Firm*—Jeffrey M. Greenman

[57] ABSTRACT

Substantially spherical polymer particles containing a colloidally, stably and uniformly dispersed magnetically responsive substance of about 5 nm to about 500 nm in diameter provide a superparamagnetic reagent carrier. Preferably, the polymer particles have a hydrated diameter of about 0.5 to 100 um, the polymer is a non-ionic cross-linked polyacrylamide gel and the magnetically responsive substance is iron oxide granules. The magnetically responsive substance may be present in an amount so that the polymer particles have a specific gravity of between 1.2 and 2.7. The reagent carrier is prepared by swelling polymer particles in a solution of iron salt so that substantially all of the iron salt solution is taken upon by the polymer particles and then converting the iron salt in situ to insoluble colloidally dispersed iron oxide granules. Converting of the iron salt may be carried out by reacting the iron salts with a base to form iron hydroxide and subsequently converting the hydroxide by heating to iron oxide. The polymer particles are particularly useful as a reagent carrier in automated immunoassays. Enzymes, antibodies, antigens or haptens may e coupled to the polymer particles.

8 Claims, No Drawings

POLYMER PARTICLES CONTAINING COLLOIDAL IRON OXIDE GRANULES FOR USE AS A MAGNETICALLY RESPONSIVE REAGENT CARRIER

This application is a continuation of application Ser. No. 07/676,010, filed Mar. 27, 1991, which is a continuation of application Ser. No. 07/053,562, filed May 21, 1987, both now abandoned.

BACKGROUND OF THE INVENTION

1. Field of the Invention

This invention relates to novel magnetically responsive particles, useful as reagent carriers More particularly, the invention relates to magnetically responsive particles which can be coupled to or otherwise associated with, reactive groups, such as enzymes, haptens or antibodies, and used as carriers for analytical reagents and to the use thereof in performing assays. Also, a method is described for preparing the reagent carriers.

2. Brief Description of the Prior Art

A variety of magnetically responsive or attractable particles have been produced by several methods which incorporate magnetite, ferrite, chromium oxide or nickel powders into matrices to which reagents can be subsequently coupled In one such method, a magnetically responsive powder is suspended in a solution of a polymer which is then gelled or precipitated to form a solid mass The solid so obtained is ground or milled to obtain an insoluble powder in which ferromagnetic granules are immobilized. See, for example, Robinson et al, *Biotechnol Bioeng* 15:603 (1973) and *Pourfarzaneh et al, Methods of Biochemical Analysis*, 28:281-3 (1982). The resulting particles are mostly oblong, jagged and of irregular size and shape. Thus, these particles exhibit poor flow properties. In addition, the number and mass of magnetic granules in individual particles are uncontrolled.

Another method involves the deposition of polymeric coatings on ferromagnetic powders by coacervation; for example, by the deposition and subsequent cross linking of albumin onto barium ferrite or magnetite See Ithakissios, et al, *Clin Chem.*, 23:2072 (1977) and Widder et al, *Clin Immunol and Immunopathol.*, 14:395-400 (1979) Other approaches to polymer-coated particles use polymerization, e.g., of acrylamide and/or methacrylamide with crosslinkers in the presence of magnetite, in a two phase (water/oil) system Also, magnetite particles themselves have been used as redox polymerization initiators. See Kronick et al, *Science*, 200:1074 (1978).

The traditional methods for producing such particles have relied on ferromagnetic powders or particles The particles generally exceed the critical size of a magnetic domain and, therefore, possess a substantial magnetic remanence Remanence is the magnetic induction that remains in a material after removal of the magnetizing force It is this property which causes such particles to remain aggregated, even in suspensions, after a magnetic field, to which they have been exposed, is removed Such particles are often spontaneously aggregated by the ambient terrestrial magnetic field. Hence, these particles are unsuited for use in automated assay systems which measure reaction rates, rather than end points, since such measurements require the periodic resuspension and redispersion of the particles.

To avoid problems associated with magnetic remanence, several methods have been developed which use superparamagnetic, rather than ferromagnetic materials, for the particles. Superparamagnetic materials, such as "ferrofluids" exhibit a very high magnetization at saturation (over 600 Gauss) and no magnetic remanence in the absence of an external magnetic field Examples include the microencapsulation of oil-based ferrofluids (see Kakimi et al, U.S Pat. No. 4,342,739) and the polymerization of aldehydes in the presence of aqueous ferrofluids See Rembaum et al, *J. Macromolecular Science, Chemistry*, A13:603-632 (1979); Rembaum, U.S. Pat. No 4,267,234; Larsson, et al, *Biotechnology Letters*, 1 501-506 (1979); and Molday, et al, *Nature*, 268 437-438 (1977) However, due to their very small size, these particles exhibit a very slow magnetic response Further, the aqueous systems are susceptible to oxidation, so that these particles must be prepared fresh for each use or stored under an inert atmosphere.

Another such method "entraps" colloidal magnetite (a water-based ferrofluid) into or onto gel particles by prolonged contact with Sepharose beads. These particles leak iron oxide which prevents them from being useful in optical density or absorption measurements See Griffin & Mosbach, *App. Biochem and Biotech.*, 6:283-292 (1981). These particles, therefore, are unstable, in that they do not retain permanently the iron oxide entrapped therein.

Another method has been described which provides a diluted array of superparamagnetic crystals in a glassy matrix See Mansfield et al, U.S. Pat. No. 4,297,337. These particles must be kept extremely small, e.g., less than one micron in diameter, to prevent their high specific gravity causing rapid sedimentation. The magnetic force on such small particles is very weak. Therefore, the fast magnetic responsiveness necessary for automated analytical systems cannot be achieved.

Thus, in summary, although magnetically responsive carrier particles have been prepared and used as reagent carriers in immunoassay procedures, each possessed characteristics which were undesirable for and compromised their usefulness in automated immunoassay systems.

SUMMARY OF THE INVENTION

In contrast to the limitations of the carrier particles of the prior art, the present invention provides magnetically responsive carrier particles useful particularly, but not exclusively, in automated, non-isotopic immunoassays. Their smooth surface and spherical shape permit them to be pumped through long, narrow conduits, such as in continuous flow analyzers, without clogging. The particles can be caused to migrate freely in a liquid medium or to be immobilized by means of an inhomogeneous magnetic field For example, when drawing them to the side or bottom of an optical cuvette, a clear supernatant is rapidly obtained for photometric analysis. In the absence of such a magnetic field, these particles are easy to disaggregate and disperse into suspension in the liquid medium, as they exhibit extremely low magnetic remanence. The ease of repeated magnetic sedimentation and resuspension allows for reaction rates, rather than just end points to be determined. Their small size and low relative specific gravity provide a very slow sedimentation rate. This, combined with their excellent chemical and physical stability, allows assay reactions to continue over an extended time period.

Accordingly, the invention provides a stable magnetically responsive, substantially remanence-free particulate reagent carrier useful, for example, in immunoassay procedures. The particulate reagent carrier comprises particles, or beads, each formed of a water-insoluble matrix, e.g., a gel, swellable in an aqueous solution having colloidally dispersed therein superparamagnetic granules. Preferably, each matrix particle has a hydrated dimension of about 0.5 to 100 um and a smooth, substantially spherical surface having an axial ratio lower than 4:1. Preferably, the superpara-magnetic granules, e.g., iron oxides, are present in sufficient quantity to impart a specific gravity of between 1.2 and 2.7 to said hydrated particles.

The particles are prepared by a process which includes incorporating by passive transport iron compounds into substantially spherical, water-swellable crosslinked polymeric matrices, then, converting the iron compounds so-incorporated in situ to their respective iron oxides. The iron oxides remain colloidally dispersed within the polymeric matrices and impart superparamagnetic properties to the resulting particles.

The term "colloidal" as used herein designates the size range of 5 to 500 nm. Particles in this size range are generally unstable unless stabilized by electrostatic forces or by steric hindrance. The latter is provided by the polymeric gel structure surrounding the magnetic substance.

The term "magnetically responsive" as used herein refers to the capacity of the particles to migrate, relative to their surroundings, under the influence of an external inhomogeneous magnetic field.

DESCRIPTION OF THE PREFERRED EMBODIMENTS

Preferred embodiments of the present invention include a stable magnetically responsive, substantially remanence-free reagent carrier or particle and a method of its preparation. Specific terms in the following description, which refer only to a particular embodiment, are exemplary of all of the embodiments unless otherwise indicated.

Polymeric Matrix

The reagent carrier or particle comprises a polymeric matrix, in which the magnetic substance is incorporated, is water insoluble but swellable in an aqueous medium. In its swollen state, the matrix is permeable to soluble iron compounds, such as iron salts or soluble compounds of nickel and chromium In an aqueous medium close to neutral pH and at room temperature, the matrix is chemically and mechanically indefinitely stable. The matrix can tolerate extremes such as strong acids or bases for times sufficient to complete the fabrication process and also is resistant to boiling water for hours. The particle formed of such matrix is substantially spherical, having an axial ratio less than about 4:1; has a smooth, non-ragged surface. Such particle has a diameter of 0.5 to 500 um, preferably 5 to 50 um. The surface of the particle has functional groups which can be activated for coupling chemistry, to attach antibodies, antigens, haptens, enzymes and other reagents to the particle. Two parameters which have been found to be particularly important are the crosslink density of the matrix material, e.g., a gel, and the diameter of the particles. The proper choice of both determines to a large extent the performance of the overall particle.

First, the crosslink density, or the water regain, of the matrix material determines the amount of iron compounds that can be incorporated during particle preparation. The larger the water regain, because of lower crosslink density, the more iron compound is incorporated per particle. However, too weakly crosslinked matrices have inherent disadvantages. Due to the large "pores", large molecules present in the milieu can diffuse into the matrix, which may result in interferences, e.g., non-specific binding, when the matrix is used as a reagent carrier in an immunoassay. Also, such matrices, when swollen, are inherently soft and mechanically weak, easily deformed and/or abraded. During further processing, the temporarily harsh conditions of very low and high pH may cause breakage of some crosslinks, which in weakly crosslinked matrices may cause significant changes in the properties of the particles. For highly crosslinked materials, this change is insignificant. Matrix materials which show an initial water regain of 5 to 20 ml/g are particularly well suited as reagent carriers. Matrix materials of lower regain can also be used, but multiple loading of the magnetic material may be necessary, as described below The size of the particles is also important for satisfactory performance. The hydrodynamic drag on a sphere increases as the square of its diameter, while the magnetic pull, and also the gravitational force, acting on it increases as the cube of its diameter. Therefore, for fast migration within the surrounding liquid or reaction mixture, a large particle is desirable. On the other hand, to optimize the total binding surface available to couple reagents, small-sized particles are desired. Accordingly, to obtain particles which exhibit sufficient high mobility and sufficient surface area, and thus balance these requirements, particles should have a diameter of from about 3 to about 60 um, preferably 20 to 40 um, usually designated by the wet-mesh size of −400.

Regarding the composition of the matrix material, several crosslinked hydrophilic polymers have been evaluated. Some were found to have suitable properties, as described, while others did not and were useless as reagent carriers. An example of a useful material is a crosslinked polyacrylamide gel, such as Biogel (BioRad Laboratories, Richmond, CA), in which the iron oxides formed predominantly inside the gel matrix and only insignificant amounts formed on the surface or between the particles In contrast is the crosslinked polysaccharide known as Sephadex (Pharmacia Fine Chemicals, Piscataway, NJ) which for no obvious reason appears to exclude iron salts, i e , when attempting to prepare particles as described below, the iron hydroxide and/or iron oxide predominantly forms on the surface of the gel particles.

The invention provides a process of preparing magnetically responsive particles or reagent carriers using polymeric matrices. This process involves incorporating by passive transport iron compounds along with water into the spherical swellable, crosslinked polymeric matrices; converting in situ the iron salts so-incorporated to their respective iron oxides. The resulting iron oxides remain colloidally dispersed within the polymeric matrix.

The term "swellable", as used herein, intends the property of the matrix material to absorb a fluid medium, usually aqueous, with or without an accompanying increase in the volume of such material.

According to the invention, the dry gel particles are contacted with a solution of iron salts to cause the gel to swell and to introduce by passive transport the iron ions into the interior of the particle Although it is not a necessary condition, the preferred solvent is water. Anhydrous iron chlorides as well as some non-ionic compounds, e.g., iron carbonyl, are also soluble in organic solvents and can in principle be used to "load" the particles. A variety of iron salts can be used as long as a concentrated solution can be prepared. Again, for reasons of convenience, the chlorides, $FeCl_2$ and are $FeCl_3$ are preferred.

The ratio of the ferrous to ferric salts is important. While the particles prepared with ferric ions alone show negligible magnetic properties, ferrous salts yield a product of considerable magnetic susceptibility A ratio of ferric to ferrous of 2:1 yields a mixed oxide of the composition of magnetite $Fe_3O_4$. Ratios within the range of 2:1 to 1:2 all yield magnetically responsive products. Because of oxidation by air during processing, it is advantageous to use more ferrous salts than required by theory.

Ferric chloride in water and at room temperature undergoes rapid partial hydrolysis leading to super polycations which have increased size and also high positive change, both effects can cause reduced permeation of the salts into the polymeric network after short initial permeation. Consequently, even iron penetration is observed. Therefore, it is advantageous to suppress the formation of such less diffusing species by the addition of salts which stabilize aqueous solutions of ferric ions. While a concentrated (1.6 molar) solution of $FeCl_3$ turns turbid in a few hours, addition of sodium sulfite in less than 0.2 molar ratio causes the solution to stay clear, albeit deep brown-red. The loading of the gel particles with iron salts in the presence of bisulfate Yields an even and uniform product. Subsequently, in the preparation of the particles, this bisulfate is washed out.

Contacting of the mixed salt solution with the dry gel particles is done such that no intersticial liquid remains by the time the particles have swollen to their full capacity. The end-point of swelling is easily detected by the observation of a "sparkling" yellow appearance not unlike a projection sceen.

The next step in the preparation is the conversion of the iron salts to their respective iron hydroxides within the particles. To this end, the pH is raised over 7 by submerging the gel particles in an alkaline medium In principle, NaOH, $Na_2CO_3$, gaseous ammonia or other bases can be used, but the preferred one is a chilled dilute (3%) ammonia solution The ammonia is volatile and, therefore, its excess can easily be boiled off later in the preparation After prolonged stirring, the supernatant is decanted and discarded The particles are then washed with copious amounts of water and allowed to equilibrate, at each washing, for at least 30 minutes, until the final supernatant shows no alkalinity, e.g., has a pH of 7.6 or less In the next step, the mixed iron hydroxides incorporated and trapped in the gel particles are converted to oxides by heat treatment. The dark brown particles are resuspended in de-ionized water and boiled for an hour. It is during this period that the magnetic response develops, owing to dehydration of iron hydroxide within the polymer network to form iron oxide, predominantly $Fe_3O_4$. After this dehydration, the gel particles are thoroughly washed to remove all soluble materials. It can be observed through the microscope that very small amounts of iron oxide cling to the surface of the gel particles which can be removed in an ultrasonic field. Therefore, the gel particles are transferred onto a nylon mesh of about 20 um openings. By gently raising and lowering this sieve in an ultrasonic bath filled with de-ionized water, the "exomagnetite" shakes loose and falls through the screen. After several minutes of sonication, particles are harvested which have a smooth shiny surface and are very responsive to an inhomogeneous magnetic field.

An alternative method of iron oxide precipitation uses an organic base. In this procedure, the saturated swollen gel particles are washed on a glass filter with a 5% dimethyl-formamide (DMF) in acetone solvent to remove the small amounts of iron solution wetting the surface of the gel. After a short period of air drying, the organic base 4-aminomethyl piperidine is added in aqueous solution to precipitate the iron oxides inside the particles. This method leads to particles which do not have any visible iron oxides on their surface and therefore do not need subsequent purifications by ultrasonic treatment. The clean particles are then air dried or kept as a slurry in a stoppered flask.

The magnetic response of the beads can be measured simply by weighing them in a standardized vial which can be placed on top of a strong permanent magnet. The difference in weight with and without the magnet in place is designated as "pull" and is compared with the pull observed with the same volume of finely ground magnetite or barium ferrite powder. Using the procedures described above, particles can easily be made which have a measured pull of at least 0.4 times that of barium ferrite and 0.20 times that of precipitated magnetite powder (Fisons Ltd , Leics U.K.). Magnetic carrier particles with this kind of susceptibility are able to exhibit a migration rate of over 5 mm/second under the influence of a strong magnetic force in a medium of one centipoise viscosity.

If an even higher magnetic mobility is desired, there are two techniques available to accomplish this. The first, termed "multiple loading", increases the magnetic force acting on each particle. The second, termed "roasting", decreases the hydrodynamic drag acting on the particles. Although the particles tend to become aggregated by the magnetic field, and aggregates move faster in the inhomogeneous magnetic field than do the individual particles, both techniques increase the rate at which the particles can be magnetically moved in the surrounding solution.

The magnetic particles prepared pursuant to the method described below contain typically 20% iron oxide (or 15% Fe). although this concentration imparts a remarkably high mobility in a magnetic field to the particles, this with iron salts. For example, the particles, formed as described above, may be finally dehydrated by acetone followed by air drying or drying in a stream of nitrogen. These dry particles can be subjected again, one or more times, to the complete process, as described. The resulting magnetic susceptibility of the final particles is considerably higher and more so for a triple-loaded material. In this process of multiple loading, the diameter of the particle is kept constant (same hydrodynamic drag) but the magnetic response of each particle is increased by virtue of its increased iron oxide content. After multiple loading, the iron oxide may constitute 50% or more by weight of the particle Another method, referred to as "roasting", increases the magnetic-hydrodynamic mobility by decreasing the hydrodynamic drag at constant force acting on the particle. This is accomplished by introducing added crosslinks into the gel in the weakly swollen or unswollen state. For example, polyacrylamide eliminates ammonia on heating above 200° C. to form imides. Both interchange and intrachain eliminations are possible (to diacrylimide bridges and/or to glutarimides, respectively), both tending to reduce the swelling capacity of the polymer. Intrachain elimination reduces the hydrophilicity and flexibility of the chains. Interchange elimination reduces the volume to which the gel particle expands on swelling. The result is a particle which is more mobile in a magnetic field than its precursor, because of reduced drag as a consequence of smaller diameter. If roasting is performed on particles not previously polished by sonication, the reaction causes fusion of the external iron oxide to the surface of the particles. The so-generated oxide-rich surface can then be used for the chemical activation of the particles for coupling. Reference is made to Example III, hereafter Magnetically-Responsive Reagent Particles The particles of the invention can be associated with a variety of reactive groups to provide a reagent, particularly, but not exclusively, useful in automated non-isotopic immunoassays. These particles carry reactive sites predominantly on their surface and can be caused either to migrate or to be immobilized at will by means of an inhomogeneous magnetic field. In the absence of such a magnetic field, these particles are easy to disperse and to resuspended in a surrounding medium because of their very low magnetic remanence and, by virtue of their small size and low relative specific gravity, their sedimentation rate is low.

While magnetically responsive reagent carriers are known in the art, none have exhibited features comparable with those of the particles of this invention, so as to be particularly useful in automated immunoassays. Because the particles have a spherical smooth surface, they can be pumped through long narrow tubes, e.g., having internal diameters of less than 1 mm, without clogging, as are required in continuous-flow analyzers such as disclosed in U.S. Pat. 4,141,687 assigned to a common assignee). These particles, when magnetically sedimented, leave a clear supernatant and, therefore, do not interfere with the colorimetric response of the assay. Further, because of their low magnetic remanence, in the absence of a magnetic field, the particles can be redispersed or resuspended in the supernatant by gentle shaking, permitting reaction rate (rather than just end point) determinations through repeated cycles of magnetic sedimentation and resuspension in the supernatant.

While a variety of reactive groups can be coupled to the surface of said particles, the primary interest lies in either catalytic moieties (e.g., enzymes) or immunologically active ligands such as antibodies, antigens or haptens.

The particles, when coupled to haptens, can be used advantageously in a one-step extraction of specific antibodies from a suspension, e.g. ascites fluids, by stirring them into the suspension and then drawing them out by an inhomogeneous magnetic field. This simple operation replaces, therefore, centrifugation or filtration followed by an affinity chromatography.

The particles can also be advantageously used to recover specific chemicals (e.g., valuable or toxic ions) from suspensions containing other particulate solids, which precludes chromatographic separation Any such chemicals can be recovered by coupling ligands to the particles of this invention which complex with these specific chemicals. Once complexed, these specific chemicals can be magnetically separated and retrieved.

The following working examples describe experiments which were performed in developing the present invention. Standard, commercially available reagent grade chemicals were used whenever possible.

EXAMPLE I

This example presents a step-by-step preparation of magnetically responsive particles in accordance with the invention, that have improved properties, making them particularly useful for automated immunoassays.

A solution of 43.5 g of $FeCl_2.5 H_2O$, 30.0 g of $FeCl_3.6 H_2O$ and 4.5 g of $Na_2S_2O_5$ was prepared in 57 mL of de-ionized water. This solution was reddish brown and limpid (density 1.39), and contained about 37% solids; $Fe^{2+}:Fe^{3+}=2:1$.

A 90 mL portion of this solution was added to 60 g of dry spherical polyacrylamide particles (Bio-Gel P-4 Extra Fine, BioRad, supra) in a beaker and gently stirred for 30 minutes. The solution was heated slowly in a water bath to 55° C. and continually stirred to ensure uniform rate of particle swelling. As the solution was taken up by the swelling particles, stirring became more difficult until finally the brown mass turned bright yellow, signaling that the intersticial liquid has vanished. Stirring was maintained until the particles were free flowing. Then, the beaker was removed from the bath and cooled to room temperature.

The swollen particles so-prepared were added to 900 mL of a 3% ammonium hydroxide solution chilled to below 5° C. in a large glass beaker and continually stirred Ice was added to maintain the temperature around 5° C. After 30 minutes, the supernatant was decanted. The particles, which had turned dark greenish-brown, were washed six times with de-ionized water, allowing each time about 30 minutes for equilibration, to remove the excess ammonia and ammonium chloride.

After washing, the solids were suspended in 1 5 liters of de-ionized water and the suspension was brought to a boil with frequent stirring. Boiling was maintained for 60 minutes. The brown color of the particles gradually turned to black. The magnetic properties had now developed, as could be seen by placing a strong magnet to the wall of the beaker After boiling, the particles were washed again with water at room temperature to remove all soluble material. Decantation was facilitated by the magnetic properties of the particles. After several washes, the boiling cycle and wash cycle were repeated and the particles were dispensed into a glass cylinder closed off at its bottom by a nylon screen of 20 um openings (Nytex-3).

The cylinder was lowered into an ultrasonic bath containing de-ionized water and, while sonicating, the cylinder was slowly raised and lowered causing the water to pass in and out of the glass cylinder through the screen. Loose iron oxide which formed in small amounts (a few percent of total) on the surface of the particles fell through the screen and was visible by its dark color. Microscopic examination showed that the originally dull-surfaced brown particles had become shiny, uniformly brown and transparent.

The final particles were air dried and weighed. The increase of weight, due to colloidal iron oxide trapped in the gel matrix, amounted to 25% of the original dry particle, or approximately 20% of the final particle. The magnetic susceptibility was determined by measuring the weight increase of a standard volume of the particles in a strong inhomogeneous magnetic field. Compared with pure precipitated magnetic iron oxide (Fison's Ltd., supra), the carrier was 0.25 times as susceptible. Fully water swollen particles had a specific gravity of about 1.35.

For even higher magnetic susceptibility, the whole process was repeated several times. It was possible to increase the magnetic force by a factor of 2.8 by doubly loading and by 3.8 by triply loading the particles. The multiply loaded particles have a considerably higher specific gravity which manifests itself in a higher sedimentation rate.

EXAMPLE II

This example illustrates a method for eliminating the formation of magnetic iron oxides on the particle surface. This is accomplished by washing traces of the iron salts from the surface of the particles, prior to treatment with base, with a solvent which does not extract the iron salts from the interior of the swollen particle.

A stock solution of iron salts was prepared from 400 g $FeCl_3.6\ H_2O$, 200 g $FeCl_2.4\ H_2O$ and 600 mL distilled water. An 80 mL portion of this solution was added to 10 g polyacrylamide particles (P-4, −400 mesh from BioRad, supra) and heated to 50° C. for 30 minutes to swell the particles. The suspension was transferred to a sintered glass funnel of medium pore size and excess solution was removed by suction. The particles were then washed with 100 mL solution of 5% dimethylformamide (DMF) in acetone, followed by four washes with 50 mL of the same solution. Then 50 mL of an aqueous solution of 10% 4-aminomethyl piperidine were added After stirring for ten minutes, the particles were washed three times with 100 mL 0.001N NaOH solution and boiled in the last wash for 30 minutes. The particles were then washed again with distilled water and air dried. The surface of the particles, so prepared, was free of any adhering iron oxides. Thus, this method avoids the need for purification of the particles by sonication.

The carrier particles of Examples I and II exhibited no physical or chemical degradation over extended periods, i.e., greater than six months. Hence, these particles define a stable reagent carrier.

EXAMPLE III

The mobility in a surrounding liquid medium of the particles of the invention can be increased by reducing their diameter while maintaining their iron content. This example demonstrates a method for introducing additional crosslinking in the gel particle in the unswollen state.

A 20 g portion of gel particles, prepared as described in Example II, was introduced into a 500 mL flask, to which 20 glass beads, 6 mm in diameter, were added. The flask was mounted on a rotary evaporator with the condenser removed and immersed in a silicon oil bath heated to above 250° C. for 2 hours, while maintaining slow rotation. The glass beads prevented the gel particles from clumping or aggregating. Ammonia evolved, indicating the formation of additional crosslinks in the gel particles. The resulting particles do not swell appreciably in aqueous solution. Their magnetic response under water, on a volumetric basis, is up to 4 times greater than the same particles which were not so-treated

EXAMPLE IV

This example demonstrates that the particles of the present invention exhibit a relatively high magnetic permeability with very low magnetic remanence.

The gel particles, prepared by Example I, were placed in a cylindrical tube. The tube was placed in a magnetic field of 3000 ampere-turns and the resulting magnetic induction was measured with a Bell gaussmeter. (The field applied was not strong enough to cause saturation). When the generating current of the solenoid was shut off, the magnetic remanence was measured on the gaussmeter. The following table shows that the ratio of the remanent flux density (remanence) to the permeability (at 3000 ampere-turn field) is negligible in the case of the particles of this invention compared with the other particles tested. The comparison of the disclosed particles, when dry and when swollen, shows that the colloidal magnetite generated therein is essentially free to rotate when the gel is swollen, while partially hindered from rotation when the gel is dried.

The swellable characteristic of the cross-linked polymeric matrix enables the matrix to absorb liquid thereby creating in its interior a liquid luke environment in which the colloidal iron oxide can perform rotational diffusion due to thermal motion present at ambient temperatures, but is prevented from transactional migration by the polymeric network. This rotational mobility of the magnetic centers results in the desirable vanishing low magnetic remanence as shown in the following table.

| Sample | Mag. Flux Density (Gauss) | Permeability | Remanence (Gauss) | Rem Perm |
|---|---|---|---|---|
| Air | 470 | $\mu_o \equiv 1.0$ | 0.0 | 0 |
| Steel (hardened) | 6200 | 13.19 | 400 | 30.3 |
| Steel | 6800 | 14.47 | 95 | 6.55 |
| Iron | 6800 | 14.47 | 57 | 3.94 |
| Magnetite powder | 950 | 2.02 | 75 | 37.13 |
| Barium Ferrite | 640 | 1.36 | 26.8 | 19.70 |
| Dry particle | 570 | 1.21 | 9 | 7.44 |
| Swollen particle | 510 | 1.09 | 1.5 | 1.37 |

EXAMPLE V

This example demonstrates the immobilization of an enzyme on the surface of the particles of this invention in such a way that its enzymatic activity is maintained:

In a 50 mL flask, 1.5 grams of air dried, triply loaded gel particles were dispersed in 25 mL toluene containing 10 mL of acetone. Also, 30 mg of polyethylenimine (Dow-P1000) was added as a 2% solution in toluene. The 50 mL flask containing the suspension was slowly rotated and gradually heated to 70° C. A gentle stream of nitrogen was used to gradually remove the acetone. As the polarity of the solvent diminishes, the polyethylenimine (PEI) adsorbs to the surface of the particles. The so-deposited PEI was then crosslinked with 3 mg of ethylenebromide at 65° C. in two hours. The particles were then filtered off, washed with acetone and dried in a stream of nitrogen.

The activation of the surface was accomplished by treating 200 mg of the PEI-coated particles with a reagent consisting of 2 mL phosphate buffer (pH =7.4) and 0.1 mL of 0.5g glutaraldehyde in 5 mL isopropyl alcohol (Baker reagent grade). After shaking the suspension for 45 minutes at room temperature, the supernatant was discarded and the particles washed twice with 1 mL each of phosphate buffer.

Coupling of beta-galactosidase to the activated particles was accomplished by dissolving 20 mg of the enzyme (Sigma G5635-750 U/mg) in 0.5 mL of the same buffer and shaking the solution with the activated particles at 2° C. for 3½ hours before storing for 18 hours at 2° C. The particles were then washed with copious amounts of cold buffer, until no enzymatic activity could be detected in the supernatant. The washed enzymatically active, magnetically responsive particles were stored in the same buffer at 4° C.

To determine if the coupled enzyme had maintained its activity, 2 mg particles were introduced into an optical cuvette having an optical path length of 7 mm and 250 uL of a substrate (ortho-nitro phenlyl galactoside, 600 mg/L in pH =7.5 phosphate buffer) were added. The particles were resuspended by shaking between successive readings. Prior to each reading of optical density at 420 nm wavelength, the reagent particles were drawn to the bottom of the cuvette by a permanent magnet. Readings were taken every 24 seconds. The color of ortho-nitrophenol developed rapidly. The initial rate of color development was greater than 300 mA/min. In the absence of reagent particles, no such color developed.

EXAMPLE VI

This example demonstrates the immobilization of an anti-body on the surfaces of particles of this invention. a suspension of 170 mg of particles, as described in Example III, in 20 mL toluene was prepared and silanized with 5 mL glycidoxypropyltrimethoxy silane (aldrich chem, Co. #23,578-4) by refluxing overnight. The particles were then washed with toluene and subsequently with acetone and dried. The activated particles wee shaken for 3 days at room temperature with 10 mL of a solution of 400 uL of a precipitated IgG fraction containing 35 mg/mL of goat-anti-rabit antibody (Antibodies, Inc.), in phosphate buffer pH 8.0. the preparation was then washed three times with 10 mL each of the same buffered and subsequently reacted with 0.1% aqueous ethanolmine for 4 hours at room temperature for deactivation of unreacted epoxy groups on the particles. The particles were then washed three times with 10 mL portions of the same buffered and subjected to a thyroxine ($T_4$) assay protocol. In this assay, 50 uL of a suspension (25 mg/mL) of the particles wee incubated with 20 uL of sample (serum), 50 uL of $T_4$-conjugate ($T_4$-beta-galactosidase) and 50 uL of first antibody (anti-$T_4$ rabbit antisrum) for 15 minutes at 37° C. in an optical cuvette. The magnetic reagent was magnetically sedimented and the supernatant discarded. The wash cycle was repeated once again using 1 mL of buffer. The particles were then suspended in the enzyme substrate of 500 uL of an orthonitrophenyl galactoside and, after 10 minutes at 37+ C., 500 uL of molar sodium carbonate were added. The suspended particles were magnetically sedimented to the bottom of the cuvette and the absorption of the supernatant was measured at 420 nm wavelength. The amount of $T_4$-beta-galactosidase bound to the particles was calculated and compared with a commercial product of similar configuration. Such commercial product was a cellulose-based solid phase sold by Technician Instruments Corporation, the common assignee, under Part No. T01-1059. The fraction of the enzyme bound to the solid phase was comparable for both, i.e., between 34% and 35%. However, the non-specific binding (NSB) as determined in the absence of the first antibody was only a fraction of that found with the commercial product.

We claim:

1. A process for preparing a stable superparamagnetic particulate reagent carrier having high magnetic permeability and low magnetic remanence comprising the steps of: a) providing a water-insoluble swellable substantially spherical and essentially non-ionic polyacrylamide gel matrix; b) contacting said polyacrylamide matrix with a solution of soluble iron salts whereby substantially all of said iron salt solution is taken up by said polyacrylamide matrix, said matrix becomes swollen, and said soluble salts pass into said polyacrylamide hel matrix; c) converting the iron salts to insoluble iron oxide granules having a diameter of from about 5 nm to 500 nm whereby a colloidally and stably dispersed magnetically responsive moiety is generated in situ within said polyacrylamide gel matrix and entrapped therein, said entrapped iron oxide essentially free to rotate within said matrix under the influence of a magnetic field and thermal motion; and d) washing the polyacrylamide gel matrix to remove soluble by-products.

2. The process of claim 1, wherein the step of converting said iron salts comprises reacting said iron salts with a base to form iron hydroxides and subsequently converting said iron hydroxides by heating to iron oxide granules.

3. The process of claim 1, comprising the additional steps of: e) drying the polyacrylamide matrix containing said iron oxide granules; and f) heating them to elevated temperatures to increase the cross-link density of the polyacrylamie matrix, thereby reducing their swelling capacity when exposed to water or aqueous solutions.

4. A stable superparamagnetic regent carrier prepared by the process of claim 1.

5. The reagent carrier of claim 4, wherein said iron oxide granules are dispersed in the matrix in sufficient quantity to impart a specific gravity of about between 1.2 and 2.7 to said reagent carrier.

6. The reagent carrier of claim 4, wherein the colloidally dispersed iron oxide granules have a diameter smaller tan about 50 nm.

7. The reagent carrier of claim 4, wherein said iron oxide granules are at lest about 20% by weight of said reagent carrier.

8. The reagent carrier of claim 4, wherein a reagent component is immobilized on the surface of said matrix.

* * * * *

UNITED STATES PATENT AND TRADEMARK OFFICE
CERTIFICATE OF CORRECTION

PATENT NO. : 5,206,159
DATED : April 27, 1993
INVENTOR(S) : Beri Cohen, et al.

It is certified that error appears in the above-identified patent and that said Letters Patent is hereby corrected as shown below:

On the title page: "Related U.S. Application Data," item [63]: should read as follows --

Continuation of Ser. No. 676,010, Mar. 27, 1991, abandoned, which is a continuation of Ser. No. 53,562, May 27, 1987, abandoned, which is a continuation of Ser. No. 667,514, Nov. 1, 1984, abandoned. --

Signed and Sealed this

Twenty-seventh Day of September, 1994

Attest:

BRUCE LEHMAN

Attesting Officer

Commissioner of Patents and Trademarks